United States Patent [19]
Kokubo et al.

[11] Patent Number: 5,700,929
[45] Date of Patent: Dec. 23, 1997

[54] BASE FOR COATING SOLID ENTERIC PHARMACEUTICAL PREPARATIONS

[75] Inventors: Hiroyasu Kokubo; Katsuyoshi Minemura, both of Nakakubiki-gun, Japan

[73] Assignee: Shin-Etsu Chemical Co., Ltd., Japan

[21] Appl. No.: 638,589

[22] Filed: Apr. 29, 1996

[30] Foreign Application Priority Data

May 1, 1995 [JP] Japan ................................ 7-107347

[51] Int. Cl.$^6$ ................................ C08B 3/00; A61K 9/28
[52] U.S. Cl. ................................ 536/63; 536/56; 536/58; 536/63; 536/115; 536/119; 514/963; 514/970; 514/47; 424/464; 424/474
[58] Field of Search ................................ 536/56, 58, 63, 536/115, 119; 514/963, 970, 47; 424/474, 464, 465

[56] References Cited

U.S. PATENT DOCUMENTS 4,983,401  1/1991  Eichel et al. ................................ 424/473

OTHER PUBLICATIONS

Adams, "Influence of Dissolution Media pH on the Release Characteristics of Aspirin Tablets coated using completely dissolved Cellulose Acetate Trimellitate (CAT), and Hydroxypropylmethy cellulose Phthalate (HPMP) Enteric Coating Materials", Pharm. Res. 1990, 7, Suppl., 598) (month not available).

Kane et al., "Technological Evaluation of three Enteric Coating Polymers I. with an Insoluble Drug," Drug Dev. and Industrial Pharm. 1993, 19, 2011–2020, (month not available).

*Primary Examiner*—John Kight
*Assistant Examiner*—Friednich N. Burnett
*Attorney, Agent, or Firm*—Parkhurst, Wendel & Burr, L.L.P.

[57] ABSTRACT

A coating base for solid enteric pharmaceutical preparations having a dissolution pH ranging from 3.5 to 4.5 essentially consisting of hydroxypropylmethyl cellulose trimellitate obtained by substituting water-soluble hydroxypropylmethyl cellulose having 1.1 to 1.6 methoxy group per glucose ring thereof with 0.2 to 1.0 trimellitate group per glucose ring, or obtained by substituting water-soluble hydroxypropylmethyl cellulose having 1.7 to 2.1 methoxy groups per glucose ring thereof with 0.2 to 0.5 trimellitate group per glucose ring. The coating base can be dissolved at the upper portion of the small intestine without delay and a solid enteric pharmaceutical preparation provided with a coating film of the base can completely release the drug included therein before the preparation passes through the small intestine. Therefore, the base can ensure a high pharmacological action of the drug.

6 Claims, No Drawings

BASE FOR COATING SOLID ENTERIC PHARMACEUTICAL PREPARATIONS

BACKGROUND OF THE INVENTION

The present invention relates to a base for coating a solid enteric pharmaceutical preparation which is dissolved in the intestine and shows its pharmacological action therein.

The solid enteric pharmaceutical preparation is provided with an enteric coating which can protect a drug having low resistance to acids from the attack of the gastric juice and simultaneously protects the gastric mucous membrane from the action of the drug and which is not dissolved till it reaches the intestine and accordingly, the drug exhibits its effect within the intestine. As an example of the base for coating a solid enteric pharmaceutical preparation, there has been known a cellulosic polymer. Specific examples thereof include cellulose acetate phthalate, cellulose acetate trimellitate, hydroxypropylmethyl cellulose phthalate, hydroxypropylmethyl cellulose acetate succinate and carboxymethylethyl cellulose.

A coating liquid has in general been prepared by dissolving the cellulosic polymer in an organic solvent or preparing an aqueous latex or an aqueous dispersion from the cellulosic polymer. Moreover, a solid enteric pharmaceutical preparation is prepared by coating a drug with the coating liquid and then drying the coated drug to form a film thereon.

These cellulosic polymers have a dissolution pH ranging from 5 to 7. The dissolution pH herein means the pH range of a solution in which the cellulosic polymers can be solubilized. If the dissolution pH ranges from 5 to 7, a solid enteric pharmaceutical preparation passes through the intestine prior to the complete release of the drug included therein because of low solubility of the cellulosic polymers. To ensure the complete release of the drug from a solid enteric pharmaceutical preparation, the solubility of the cellulosic polymers should be improved by reducing the dissolution pH thereof.

Remington's Pharmaceutical Sciences, 13th ed., p. 604, Mack Publishing Co. (1965) discloses that a polymer carrying, in the molecule, carboxyl groups and hydrophobic groups can be dissolved in a solvent having a specific pH value through dissociation of the carboxyl groups thereof. Therefore, the solubility of a particular cellulosic polymer can arbitrarily be controlled by properly adjusting the degree of substitution of the polymer with these substituents. For instance, commercially available hydroxypropylmethyl cellulose acetate is a hydroxypropylmethyl cellulose substituted with carboxyl groups (succinoyl groups) and hydrophobic groups (acetyl groups). In this case, the solubility of the cellulosic polymer can be controlled by appropriately adjusting the degrees of substitution with succinoyl groups and acetyl groups.

Japanese Patent Application Publication No. 48-19391 discloses cellulose acetate can be reacted with a dibasic carboxylic acid (such as phthalic acid) to prepare cellulose acetate phthalate which has a dissolution pH of 5.5, while cellulose acetate can be reacted with a tribasic trimellitic acid which has a high degree of dissociation and low hydrophobicity to prepare cellulose acetate trimellitate which has a dissolution pH of 5.0. This patent further discloses that hydroxypropylmethyl cellulose can be reacted with trimellitic acid to give hydroxypropylmethyl cellulose trimellitate whose dissolution pH is 4.5.

As has been discussed above in detail, there have been known several means for reducing the dissolution pH of cellulosic polymers. However, the cellulosic polymers having the foregoing dissolution pH values do not allow the drug contained in a solid enteric pharmaceutical preparation to show its pharmacological action since the preparation passes through the intestine before it does not completely release the drug included therein.

To ensure sufficient pharmacological action of a drug, it is necessary to further reduce the dissolution pH values of cellulosic polymers as the coating bases and to ensure immediate dissolution of the cellulosic polymers at the upper portion of the intestine.

There has been investigated, as a means for further reduction of the dissolution pH of the coating base, a method for preparing hydroxypropylmethyl cellulose acetate maleate having a dissolution pH falling within the range of from 3 to 4, which comprises substituting a water-soluble cellulose ether with acetyl and maleyl groups. However, the dissolution pH of hydroxypropylmethyl cellulose acetate maleate is determined by the foregoing two kinds of substituents and therefore, the control thereof is very difficult. Moreover, moisture can easily penetrate into the solid preparation through the enteric coating film because of highly water-soluble nature of maleyl groups and accordingly, hydroxypropylmethyl cellulose acetate maleate is not a preferred base for coating drugs to form solid enteric pharmaceutical preparations.

SUMMARY OF THE INVENTION

The present invention has been developed for eliminating the foregoing drawbacks associated with the conventional techniques and accordingly, it is an object of the present invention to provide a base for coating solid enteric pharmaceutical preparations, which permits the improvement in the pharmacological action of the drugs contained therein.

The foregoing object of the present invention can effectively be accomplished by providing a base for coating a solid enteric pharmaceutical preparation, essentially consisting of a hydroxypropylmethyl cellulose trimellitate which is prepared by substituting a water-soluble hydroxypropylmethyl cellulose carrying 1.1 to 1.6 methoxy group per glucose ring thereof, with 0.2 to 1.0 trimellitate residue per glucose ring. The coating base has a dissolution pH ranging from 3.5 to 4.5.

If the number of methoxy groups is less than 1.1, it is difficult to dissolve the hydroxypropylmethyl cellulose in an organic solvent and this makes the preparation of a coating liquid containing the same difficult. On the other hand, if it exceeds 1.6, the resulting cellulose has a dissolution pH of not less than 4.5. Moreover, if the number of substituted trimellitate groups is less than 0.2, the hydrophobicity of the resulting film due to the presence of trimellitate groups becomes insufficient. Therefore, moisture easily penetrates into the solid enteric pharmaceutical preparation provided with the film of the cellulose and the resulting cellulose does not exhibit sufficient resistance to acids required for the coating base. Moreover, if it exceeds 1.0, the resulting cellulose has a dissolution pH of not less than 4.5.

According to another aspect of the present invention, there is provided a base for coating a solid enteric pharmaceutical preparation essentially consisting of a hydroxypropylmethyl cellulose trimellitate, which is prepared by substituting a water-soluble hydroxypropylmethyl cellulose carrying 1.7 to 2.1 methoxy groups per glucose ring thereof, with 0.2 to 0.5 trimellitate group per glucose ring. The coating base has a dissolution pH ranging from 3.5 to 4.5.

If the content of methoxy groups is beyond the range defined above, the solid enteric pharmaceutical preparation coated with the base cannot be used in medical treatments. Moreover, if the number of trimellitate group is less than 0.2, the hydrophobic nature of the resulting coating film due to the presence of trimellitate groups becomes insufficient. Therefore, moisture easily penetrates into the solid enteric pharmaceutical preparation provided with the coated film and the resulting cellulose does not exhibit sufficient resistance to acids required for the coating base. Moreover, if it exceeds 0.5, the resulting cellulose has a dissolution pH of not less than 4.5.

The degree of substitution of the hydroxypropoxy groups on these hydroxypropylmethyl cellulose is preferably not less than 0.03 per glucose ring of the cellulose. This is because if it is less than 0.03, the trimellitic acid ester groups are liable to undergo hydrolysis.

The viscosity of a 2% by weight aqueous solution of hydroxypropylmethyl cellulose preferably ranges from 3 to 10 cP. If the viscosity thereof is less than 3 cP, the coating film ultimately formed on a drug to give a solid enteric pharmaceutical preparation has insufficient strength, while if the viscosity is higher than 10 cP, the cellulose gives a solution having an extremely high viscosity when dissolved in a solvent prior to subjecting it to a reaction for forming a coating film and this makes the handling of the solution inconvenient.

DETAILED DESCRIPTION OF THE INVENTION

Specifically, methods for preparing hydroxypropylmethyl cellulose trimellitate used as the coating base are as follows. First of all, hydroxypropylmethyl cellulose is reacted with trimellitic anhydride in a specific rate. This substitution reaction is terminated by the addition of purified water to the reaction system and then cooling the same. After the completion of the substitution reaction, an acid (a mineral acid such as hydrochloric acid or sulfuric acid) is added to the reaction system, followed by pouring the reaction solution into a large excess of water to thus sufficiently precipitate hydroxypropylmethyl cellulose trimellitate formed. After sufficiently washing, with purified water, the resulting cellulose trimellitate till the wash liquid does not show acidity any more, followed by drying the product in a fluidized bed drying machine to give a coating base whose dissolution pH falls within the range of from 3.5 to 4.5. The product may if necessary be pulverized or classified.

It would be considered that cellulose derivatives free of methoxy group such as hydroxypropyl cellulose and hydroxyethyl cellulose may likewise be used as ingredients for the coating base. However, hydroxypropyl cellulose trimellitates synthesized from the foregoing cellulose derivatives show extremely high flexibility and accordingly, it sometimes shows extreme stickiness during the coating treatment.

Moreover, it would also be considered that methyl cellulose may be used as a starting material, but the trimellitic acid ester groups of the resulting product are liable to undergo hydrolysis since methyl cellulose is free of any hydroxypropoxy group.

For this reason, hydroxypropylmethyl cellulose is most preferred as the ingredient for the coating base of the present invention.

The dissolution pH of hydroxypropylmethyl cellulose trimellitate is determined by the method as will be detailed below. First, hydroxypropylmethyl cellulose trimellitate is dissolved in an organic solvent, followed by casting the resulting solution on a glass plate to form a film having a thickness of 100 μm. The film is cut into pieces having a size of 1 cm×1 cm and then the pieces are immersed in a dissolution solvent using a support cylinder according to the Disintegration Test defined in the Pharmacopoeia of Japan to thus determine the pH value of the solvent in which the film is dissolved. Several kinds of Macluvain buffer solutions having different pH values are used as the dissolution solvents.

The coating treatment of a drug comprises the step of injecting a coating solution onto the drug and simultaneously drying the solution injected on the drug using a coating device to thus form a film thereon. The coating solution or liquid can be prepared by dissolving hydroxypropylmethyl cellulose trimellitate in an organic solvent such as acetone, methylene chloride/alcohol or alcohol/water, or by pulverizing the cellulose trimellitate into fine particles having a particle size of not more than 10 μm and then dispersing them in water. The coating solution may further comprise a variety of pharmaceutically acceptable additives such as a plasticizer, a coloring agent, a pigment and/or an antitack agent. In addition, the cellulose trimellitate may be used in combination with any known coating bases to thus control the release characteristics and solubility thereof.

Coating devices usable in the present invention include, for instance, a fluidized bed coating device, a pan coating device and a flow-through rotational drum type coating device.

As has been described above, the dissolution pH of hydroxypropylmethyl cellulose trimellitate as the coating base for solid enteric pharmaceutical preparations is determined by methoxy groups and trimellitate groups present thereon. If the dissolution pH of hydroxypropylmethyl cellulose trimellitate ranges from 3.5 to 4.0, the cellulose derivative is not dissolved in the gastric juice, but is dissolved at the upper portion of the small intestine without delay. For this reason, the solid enteric pharmaceutical preparation can completely release the drug contained therein before the preparation passes through the small intestine.

The cellulosic polymer used as the coating base for solid enteric pharmaceutical preparations according to the present invention can be dissolved at the upper portion of the small intestine without delay. Accordingly, the pharmaceutical preparation can completely release the drug contained therein before it passes through the small intestine and can thus show a high pharmacological action.

The coating base of the present invention will hereinafter be described in more detail with reference to the following non-limitative working Examples and Comparative Examples.

EXAMPLE 1

To a 5 liter biaxial kneader, there were added 700 g of a hydroxypropylmethyl cellulose whose 2% by weight aqueous solution has a viscosity of 5.5 cP (HPMC; methoxy group content: 23.3% by weight; hydroxypropoxy group content: 6.4% by weight; available from Shin-Etsu Chemical Co., Ltd.) and 2100 g of acetic acid, followed by dissolving the cellulose at a temperature of 70° C. After the completion of the dissolution, 910 g of trimellitic anhydride was added to the kneader as an esterifying agent, followed by addition of 275 g of sodium acetate as a catalyst and reaction of these reactants at a temperature ranging from 85° to 90° C. After 5 hours, the reaction was terminated by cooling the reaction system and adding 1180 g of purified water. Then 330 g of concentrated hydrochloric acid was added to the reaction solution and the resulting mixture was poured into a large excess of purified water to thus precipitate the reaction product. The product was washed with purified water till the wash liquid did not show acidity any more and dried for 2 hours in a fluidized bed drying machine maintained at a temperature of 60° C. to give hydroxypropylmethyl cellulose trimellitate.

The resulting hydroxypropylmethyl cellulose trimellitate had a DS (degree of substitution) for methoxy group of 1.44 (14.2%) and an MS (molar substitution) for hydroxypropoxy group of 0.16 (3.8%). These DS and MS values are expressed in terms of the number of each substituent introduced to the trimellitate per glucose unit.

The resulting hydroxypropylmethyl cellulose trimellitate was inspected for the dissolution pH and the amount of seepage water. These characteristic properties of the trimellitate were determined according to the following methods.

First, the cellulose trimellitate was dissolved in a 1:1 methylene chloride/ethanol mixed solvent, followed by casting the resulting solution on a glass plate to form a film having a thickness of 100 μm. Then the dissolution pH was determined according to the Disintegration Test specified in the Pharmacopoeia of Japan. The film which had been cut into pieces having a size of 1 cm square was immersed in each of several kinds of Macluvain buffer solutions having different pH values and as a result, it was confirmed that the film was dissolved in the buffer solution having a pH of 3.9.

On the other hand, the amount of seepage water was determined as follows. A film of the trimellitate having a thickness of 100 μm was fitted to a vial using a Teflon packing and then a saturated aqueous solution of common salt was introduced into the vial. The vial was allowed to stand in a desiccator in which calcium chloride had been accommodated, at 25° C. and the amount of seepage water per unit area (g/square meter ë24 hr) was evaluated on the basis of the weight change of the vial. The amount of seepage water was found to be 190 g/square meter ë24 hr.

These dissolution pH value and the amount of seepage water thus determined clearly indicate that the resulting hydroxypropylmethyl cellulose trimellitate can sufficiently be used as the coating base for solid enteric pharmaceutical preparations.

EXAMPLE 2

Hydroxypropylmethyl cellulose trimellitate was prepared by repeating the same procedures used in Example 1 except that the amounts of trimellitic acid and sodium acetate were changed to 455 g and 248 g, respectively.

The resulting hydroxypropylmethyl cellulose trimellitate was found to have a DS value for methoxy group of 1.44 (18.6%), an MS value for hydroxypropoxy group of 0.16 (5.0%) and a DS value for trimellitate group of 0.25(20.2%).

A film was prepared from the hydroxypropylmethyl cellulose trimellitate by the same method used in Example 1 and the dissolution pH thereof was determined in the same manner detailed in Example 1. As a result, it was found to be 3.8.

The result of the dissolution pH determination clearly indicates that the resulting hydroxypropylmethyl cellulose trimellitate is suitable for use as the coating base for solid enteric pharmaceutical preparations.

EXAMPLE 3

The same procedures used in Example 1 were repeated except that the amounts of trimellitic acid and sodium acetate were changed to 1500 g and 300 g, respectively to give hydroxypropylmethyl cellulose trimellitate.

The resulting hydroxypropylmethyl cellulose trimellitate was found to have a DS value for methoxy group of 1.44 (11.9%), an MS value for hydroxypropoxy group of 0.16 (3.2%) and a DS value for trimellitate group of 0.95(49.1%).

A film was prepared from the hydroxypropylmethyl cellulose trimellitate by the same method used in Example 1 and the dissolution pH thereof was determined in the same manner used in Example 1. As a result, it was found to be 4.2.

The result of the dissolution pH determination clearly indicates that the resulting hydroxypropylmethyl cellulose trimellitate is suitable for use as the coating base for solid enteric pharmaceutical preparations.

EXAMPLE 4

The same procedures used in Example 3 were repeated except that there was used, as a raw material, hydroxypropylmethyl cellulose (HPMC; methoxy group content: 29.0% by weight; hydroxypropoxy group content: 9.2% by weight; available from Shin-Etsu Chemical Co., Ltd.) and that the amounts of trimellitic acid and sodium acetate were changed to 450 g and 235 g, respectively to give hydroxypropylmethyl cellulose trimellitate.

The resulting hydroxypropylmethyl cellulose trimellitate was found to have a DS value for methoxy group of 1.90 (22.9%), an MS value for hydroxypropoxy group of 0.25 (6.5%) and a DS value for trimellitate group of 0.28(21.0%).

A film was prepared from the hydroxypropylmethyl cellulose trimellitate by the same method used in Example 1 and the dissolution pH thereof was determined in the same manner described in Example 1. As a result, it was found to be 3.5.

The result of the dissolution pH determination clearly indicates that the resulting hydroxypropylmethyl cellulose trimellitate is suitable for use as the coating base for solid enteric pharmaceutical preparations.

EXAMPLE 5

The same procedures used in Example 4 were repeated except that the amounts of trimellitic acid and sodium acetate were changed to 645 g and 245 g, respectively to give hydroxypropylmethyl cellulose trimellitate.

The resulting hydroxypropylmethyl cellulose trimellitate was found to have a DS value for methoxy group of 1.90 (20.3%), an MS value for hydroxypropoxy group of 0.25 (6.5%) and a DS value for trimellitate group of 0.45(30.0%).

A film was prepared from the hydroxypropylmethyl cellulose trimellitate by the same method used in Example 1 and the dissolution pH thereof was determined by the same method described in Example 1. As a result, it was found to be 4.5.

The result of the dissolution pH determination clearly indicates that the resulting hydroxypropylmethyl cellulose trimellitate is suitable for use as the coating base for solid enteric pharmaceutical preparations.

COMPARATIVE EXAMPLE 1

The same procedures used in Example 1 were repeated except that the amounts of trimellitic acid and sodium acetate were changed to 860 g and 260 g, respectively to give hydroxypropylmethyl cellulose trimellitate.

The resulting hydroxypropylmethyl cellulose trimellitate was found to have a DS value for methoxy group of 1.90

(18.0%), an MS value for hydroxypropoxy group of 0.25 (5.7%) and a DS value for trimellitate group of 0.65(38.3%).

A film was prepared from the hydroxypropylmethyl cellulose trimellitate by the same method used in Example 1 and the dissolution pH thereof was determined in the same manner described in Example 1. As a result, it was found to be 4.6.

It was confirmed that the resulting hydroxypropylmethyl cellulose trimellitate had a high dissolution pH value and therefore, it is insufficient for use as the coating base for solid enteric pharmaceutical preparations.

COMPARATIVE EXAMPLE 2

The same procedures used in Example 1 were repeated except that the amounts of trimellitic acid and sodium acetate were changed to 1750 g and 330 g, respectively to give hydroxypropylmethyl cellulose trimellitate.

The resulting hydroxypropylmethyl cellulose trimellitate was found to have a DS value for methoxy group of 1.44 (11.1%), an MS value for hydroxypropoxy group of 0.16 (3.0%) and a DS value for trimellitate group of 1.10(52.7%).

A film was prepared from the hydroxypropylmethyl cellulose trimellitate by the same method used in Example 1 and the dissolution pH thereof was determined in the same manner used in Example 1. As a result, it was found to be 4.7.

It was confirmed that the resulting hydroxypropylmethyl cellulose trimellitate had a high dissolution pH value and therefore, it is insufficient for use as the coating base for solid enteric pharmaceutical preparations.

COMPARATIVE EXAMPLE 3

To a 5 liter biaxial kneader, there were added 700 g of hydroxypropylmethyl cellulose whose viscosity of a 2% by weight aqueous solution was 5.2 cP (HPMC; methoxy group content: 29.1% by weight; hydroxypropoxy group content: 8.9% by weight; available from Shin-Etsu Chemical Co., Ltd.) and 2100 g of acetic acid, followed by dissolution of the cellulose at a temperature of 70° C. After the completion of the dissolution, there were added, to the resulting solution, 176 g of acetic anhydride and 193 g of maleic anhydride as esterifying agents, as well as 278 g of sodium acetate as a catalyst, followed by the reaction of these reactants at a temperature ranging from 85° to 90° C. After 5 hours, the reaction was stopped by cooling and adding 1180 g of purified water. The mixture obtained by adding 330 g of concentrated hydrochloric acid to the reaction system was poured into a large excess of purified water to thus precipitate the reaction product. The product was washed with purified water till the wash liquid did not show acidity anymore and then dried for 2 hours in a fluidized bed dryer maintained at 60° C. to give hydroxypropyl-methyl cellulose acetate maleate.

The resulting hydroxypropylmethyl cellulose acetate maleate was found to have a DS value for methoxy group of 1.90 (22.7%), an MS value for hydroxypropoxy group of 0.24 (6.9%), a DS value for acetyl group of 0.31 (5.1%) and a DS value for maleyl group of 0.45 (17.2%).

A film was prepared from the resulting hydroxypropylmethyl cellulose acetate maleate and was inspected for the dissolution pH value and the amount of seepage water in the same manner used in Example 1. As a result, it was confirmed that the film was dissolved in a buffer solution having a pH of 3.5 and exhibited an amount of seepage water of 190 g/square meter e24 hr.

The film prepared in Comparative Example 3 has an amount of seepage water greater than that observed for the film of Example 1. This is because the cellulosic polymer of this Comparative Example is prepared by substituting hydroxypropylmethyl cellulose with maleyl groups having high water-solubility. The hydroxypropylmethyl cellulose acetate maleate is thus insufficient for use as the coating base because of its high amount of seepage water.

What is claimed is:

1. A base for coating solid enteric pharmaceutical preparations having a dissolution pH ranging from 3.5 to 4.5 essentially consisting of hydroxypropylmethyl cellulose trimellitate obtained by substituting water-soluble hydroxypropylmethyl cellulose having 1.1 to 1.6 methoxy group per glucose ring thereof, with 0.2 to 1.0 trimellitate group per glucose ring.

2. The coating base of claim 1 wherein the viscosity of a 2% by weight aqueous solution of the cellulose trimellitate ranges from 3 to 10 cP.

3. The coating base of claim 1 wherein the hydroxypropylmethyl cellulose has a degree of substitution with hydroxypropoxy group of not less than 0.03 per glucose ring.

4. A base for coating solid enteric pharmaceutical preparations having a dissolution pH ranging from 3.5 to 4.5 essentially consisting of hydroxypropylmethyl cellulose trimellitate obtained by substituting water-soluble hydroxypropylmethyl cellulose having 1.7 to 2.1 methoxy groups per glucose ring thereof with 0.2 to 0.5 trimellitate group per glucose ring.

5. The coating base of claim 4 wherein the viscosity of a 2% by weight aqueous solution of the cellulose trimellitate ranges from 3 to 10 cP.

6. The coating base of claim 4 wherein the hydroxypropylmethyl cellulose has a degree of substitution with hydroxypropoxy group of not less than 0.03 per glucose ring.

* * * * *